(12) United States Patent
Croft et al.

(10) Patent No.: US 9,291,756 B2
(45) Date of Patent: Mar. 22, 2016

(54) FILTER

(75) Inventors: Daniel I. Croft, Corvallis, OR (US);
Barry T Phillips, Fort Collins, CO (US);
Brad Benson, Corvallis, OR (US); Cary G Addington, Albany, OR (US); Angus Wu, Corvallis, OR (US); Stephan R Clark, Albany, OR (US); Guy Adams, Stroud (GB); James Stasiak, Lebanon, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 223 days.

(21) Appl. No.: 13/981,938

(22) PCT Filed: Jan. 28, 2011

(86) PCT No.: PCT/US2011/000167
§ 371 (c)(1),
(2), (4) Date: Jul. 26, 2013

(87) PCT Pub. No.: WO2012/102690
PCT Pub. Date: Aug. 2, 2012

(65) Prior Publication Data
US 2013/0334441 A1 Dec. 19, 2013

(51) Int. Cl.
| | | |
|---|---|---|
| *B42D 15/00* | (2006.01) | |
| *G02B 5/20* | (2006.01) | |
| *G06F 3/03* | (2006.01) | |
| *G06F 3/0354* | (2013.01) | |
| *G01N 21/64* | (2006.01) | |
| *B82Y 20/00* | (2011.01) | |

(52) U.S. Cl.
CPC ............... *G02B 5/208* (2013.01); *G01N 21/64* (2013.01); *G06F 3/0321* (2013.01); *G06F 3/03542* (2013.01); *B82Y 20/00* (2013.01); *Y10S 977/774* (2013.01)

(58) Field of Classification Search
CPC .......... G01N 21/6428; G01N 21/6458; G01N 21/6408; G01N 21/645; G01N 21/6452
See application file for complete search history.

(56) References Cited

U.S. PATENT DOCUMENTS

| | | | |
|---|---|---|---|
| 5,882,779 | A | 3/1999 | Lawandy |
| 6,208,466 | B1 | 3/2001 | Liu et al. |
| 7,019,905 | B2 | 3/2006 | Weber |
| 2004/0038138 | A1 | 2/2004 | Kiguchi et al. |
| 2006/0290843 | A1 | 12/2006 | Epstein et al. |
| 2008/0252064 | A1 * | 10/2008 | Sekine et al. .................... 283/91 |
| 2009/0153953 | A1 | 6/2009 | Banerjee et al. |
| 2009/0279170 | A1 | 11/2009 | Miyazaki et al. |
| 2010/0001509 | A1 * | 1/2010 | Whiteman ....................... 283/91 |

(Continued)

FOREIGN PATENT DOCUMENTS

| | | |
|---|---|---|
| JP | 2008-243154 A | 10/2008 |
| JP | 2010-085532 A | 4/2010 |

OTHER PUBLICATIONS

Extended European Search Report, EP Application No. 11857345.0, May 27, 2014, pp. 1-10.

(Continued)

*Primary Examiner* — David Porta
*Assistant Examiner* — Mamadou Faye
(74) *Attorney, Agent, or Firm* — HP Inc Legal Department (57) ABSTRACT

Embodiments disclosed herein relate to a filter (100). In one embodiment, the filter includes a pattern (120). The pattern may reflect or fluoresce non-visible light.

19 Claims, 7 Drawing Sheets

(56) References Cited

U.S. PATENT DOCUMENTS

2011/0164308 A1* 7/2011 Arsenault et al. ............ 359/322
2013/0049844 A1* 2/2013 Bita et al. .................... 327/517
2013/0078576 A1* 3/2013 Wu et al. ...................... 430/296

OTHER PUBLICATIONS

International Search Report and Written Opinion received in PCT Application No. PCT/US2011/000167, mailed on Oct. 28, 2011, 9 pgs.

* cited by examiner

FILTER

CROSS REFERENCE TO RELATED APPLICATIONS

This application is a national stage application under 35 U.S.C. §371 of PCT/US2011/000167, filed 28 Jan. 2011.

BACKGROUND

In order to allow for user interaction with a display device, inductive, resistive or capacitive sensors may be integrated into the display device. However, inductive sensors are often too expensive for large displays while resistive and capacitive sensors generally do not provide sufficient resolution for more complex functions such as handwriting capture or graphic design.

Other techniques for user interaction with the display device include applying an optical pattern to a surface of the display device with an optical reader type stylus being used by the user to detect this pattern. Current patterns are usually formed from an infrared (IR) reflecting ink that reflects IR light projected by the stylus. The stylus detects the pattern based on contrast between the reflected IR light and non-reflected IR light. However, such contrast may be difficult to detect on glass or plastic surfaces of the display devices. Moreover, these patterns may degrade image quality of the display device due to these patterns blocking some visible light being emitted from the surface of the display device.

BRIEF DESCRIPTION OF THE DRAWINGS

The following detailed description references the drawings, wherein.

DETAILED DESCRIPTION

Specific details are given in the following description to provide a thorough understanding of embodiments. However, it will be understood by one of ordinary skill in the art that embodiments may be practiced without these specific details. For example, systems may be shown in block diagrams in order not to obscure embodiments in unnecessary detail. In other instances, well-known processes, structures and techniques may be shown without unnecessary detail in order to avoid obscuring embodiments.

In order to allow for user interaction with a display device, marking devices, such as an optical pen, have been developed to interact with a pattern over the display device. For example, these marking devices may be configured to emit non-visible light, such as infrared light, and the pattern over the display may be configured to reflect the emitted non-visible light that is incident on the pattern. The emitted non-visible light that is not incident on the pattern may not be reflected or have a reduced reflection compared to that of the pattern.

The marking device may further include a detector, such as an infrared camera, to detect the non-visible light reflected from the pattern. Accordingly, the detector may determine a direction and/or speed that the marking device is moved over the display device by tracking a change in position of a portion of the pattern reflecting the non-visible light. Thus, the marking device or user's hand movements over the display may be captured as data by the detector. This data may then be transmitted and interpreted for a given application, such as handwriting capture or graphic design.

However, current types of patterns for display devices are costly to manufacture or degrade image quality by blocking visible light being emitted from the display devices. Embodiments may provide patterns that are relatively low in cost and/or transmit substantially all the visible light.

Figure 1:
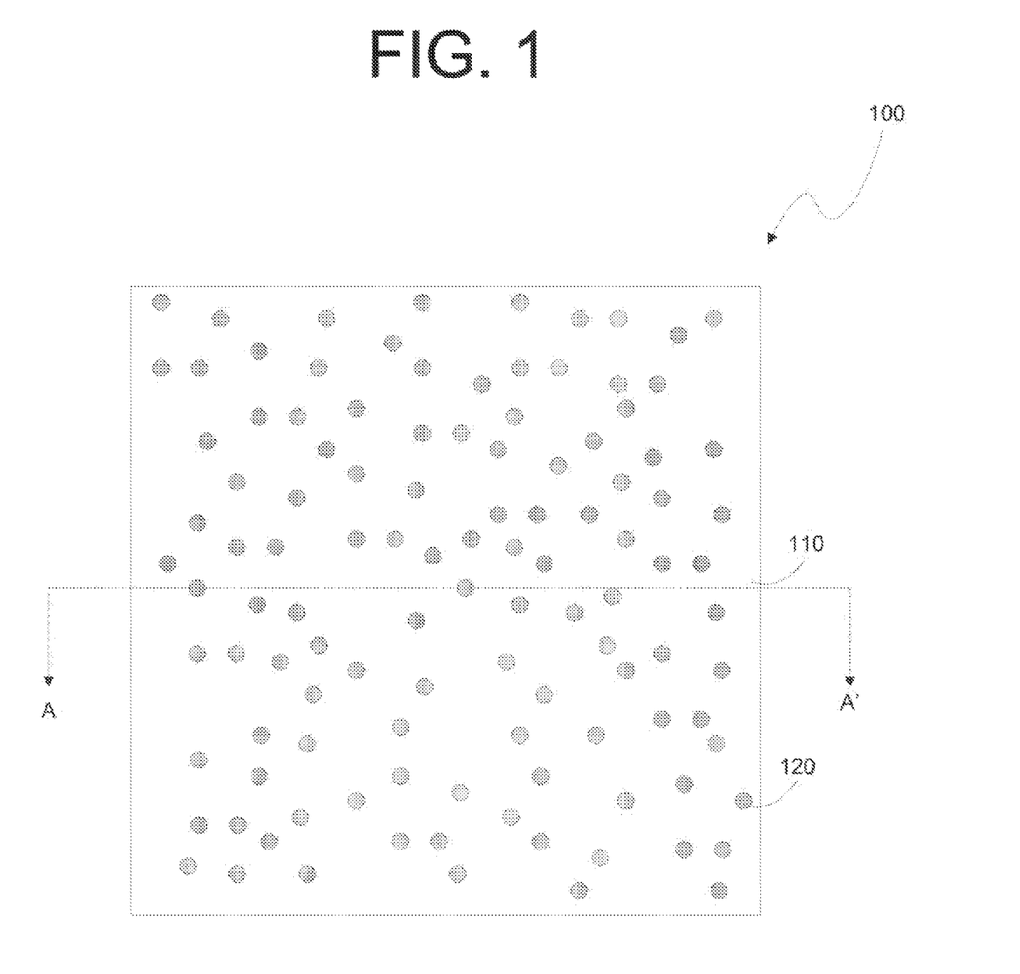
FIG. 1 is a block diagram of a top-down view of an example filter.

Referring now to the drawings, FIG. 1 is a block diagram of a top-down view of an example filter 100, where the example filter 100 may represent a portion of a larger filter. In the embodiment of FIG. 1, the filter 100 includes a substrate 110 and a pattern 120 over the substrate 110. Here, the pattern 120 is shown to include a plurality of dots. However, the pattern 120 is not limited to the dots. For example, embodiments of the pattern 120 may include any combination of dots, lines, geometric shapes, curves, and the like.

Though the pattern 120 shown in FIG. 1 includes a plurality of elements, such as the dots, embodiments of the pattern 120 may range from a single element, such as a single dot, to a higher concentration of elements or dots than that shown in FIG. 1. The dots in FIG. 1 have been arranged randomly, but embodiments of the pattern 120 may also have elements arranged uniformly or according to any other type of distribution known in the art. For example, the pattern 120 may be arranged symmetrically, asymmetrically, and the like. In addition, the pattern 120 may be repeating or non-repeating.

In FIG. 1, the pattern 120 may one of transmit substantially all visible light and fluoresce non-visible light, and the pattern 120 may reflect at least a portion of the non-visible light if the pattern 120 is to transmit substantially all the visible light, as will be described in greater detail below with respect to FIGS. 2 and 3. The term portion may refer to a part of a whole. For example, a portion of the non-visible light may refer to less than all of the non-visible light spectrum. In some embodiments, the term substantially may be greater than 97 percent (%). Further, the transmittance or reflectance by the pattern 120 may not include any air to material losses. The visible light may include a portion of the electromagnetic spectrum that is visible to the human eye and the non-visible light may include the portion of the electromagnetic spectrum that is not visible to the human eye. The term light alone may include both the visible and non-visible light. For instance, the visible light spectrum may approximately include wavelengths in the range of 390 nanometers (nm) to 750 nm. The non-visible light spectrum may generally include wavelengths less than 390 nm and greater than 750 nm. However, the wavelengths of the visible and non-visible light may somewhat overlap. For example, wavelengths as high as 400 nm and as low as 700 nm may also be included in the non-visible light spectrum. The term fluoresce may include reradiating previously absorbed light, where the reradiated light is usually of a different wavelength than the absorbed light. For example, the pattern 120 may fluoresce light at lower frequency or higher wavelength than the light absorbed by the pattern 120.

At least two of the dots of the pattern 120 in FIG. 1 may be between 0.25 millimeters (mm) and 0.5 mm apart from each other. Moreover, an average length between adjacent dots in FIG. 1 may be between 0.25 mm and 1 mm. However, embodiments may include dots less than 0.25 mm apart or greater than 0.5 mm apart. The substrate 110 may be a rigid material, such as glass, or a flexible material, such as plastic. Further, the substrate 110 may be any type of material known in the art.

Figure 2:
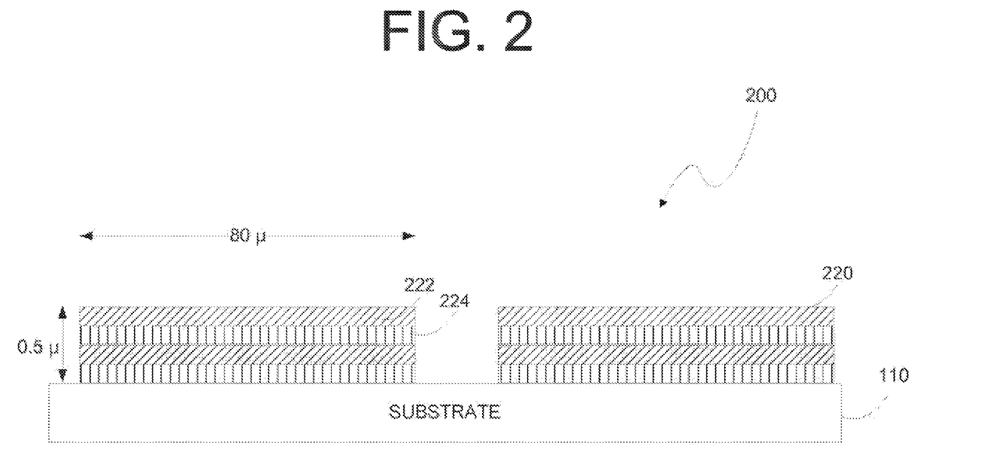
FIG. 2 is a block diagram of a cross-sectional view of an example pattern taken along the line A-A' of FIG. 1.

FIG. 2 is a block diagram of a cross-sectional view of an example pattern 220 taken along the line A-A' of FIG. 1. In the embodiment of FIG. 2, the pattern 220 includes dots formed from a plurality of stacked layers of thin film 222 and 224 over the substrate 110. The thin films 222 and 224 may be composed of dielectric material, where different types of dielectric material have different refractive indices.

Due to interference effects between incident and reflected light waves at boundaries of the thin films 222 and 224, the dots of the pattern 220 may reflect part of the light spectrum, such as the non-visible light, and transmit a remaining part of the light spectrum, such as the visible light. Further, the optical properties of the thin films 222 and 224 allow for a very low level of absorption to be generally maintained for both the non-visible and the visible light. Thus, the dots of the pattern 220 do not generally absorb the visible light and do not generally absorb the non-visible light. Also, the dots of the pattern 220 may transmit all or substantially all of the visible light and reflect all or substantially all, or at least a portion of, of the non-visible light. As explained in greater detail with respect to FIG. 7, according to the embodiment of FIG. 2, the dots of the pattern 220 may not generally block the passage of light from a surface upon which the dots of the pattern 220 are deposited, even where a density of the dots of the pattern 220 is relatively high. For example, if the dots of the pattern 220 virtually or nearly covered an entire surface of the substrate 110 according to an embodiment, substantially all of the visible light being transmitted through the substrate and facing the dots of the pattern 220 would still pass through the dots.

The stacked layers of thin film 222 and 224 are arranged to reflect the non-visible light and simultaneously pass the visible light. In FIG. 2, there are four stacked layers of thin films alternating between at least two different types of material 222 and 224. The two types of material may be any type of thin film material known in the art. For example, the two different types of material 222 and 224 may include $SiO_2$ and at least one of $TiO_2$, $Nb_2O_5$, $Ta_2O_5$, $ZrO_2$, and $HfO_2$. Depending on the type of materials used, the dots may exhibit additional properties, such as ultraviolet (UV) protection, scratch resistance, a vapor barrier, etc. Further, other embodiments may alternate between more than two types of material and may include more or less than four stacked layers of thin film.

In FIG. 2, the stacked layers of thin film 222 and 224 are shown to have a same thickness. However, other embodiments may include at least two of the stacked layers of thin film to have different thicknesses. Accordingly, by varying the thicknesses of the thin films, embodiments may vary which wavelengths of light reflect from the dots of the pattern 220 and/or which of the wavelengths of light pass through the dots.

For example, an embodiment may include at least 25 stacked layers of thin film, where each layer of thin film ranges in thickness between 25 nanometers (nm) and 120 nm. Additionally, embodiments may include other types of material and/or layers between, above or under the stacked layers of thin film.

Figure 3:
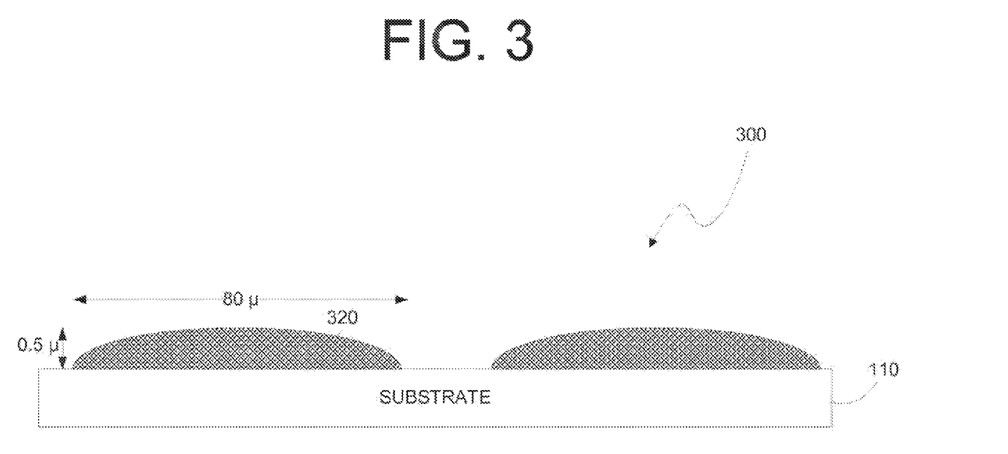
FIG. 3 is a block diagram of a cross-sectional view of another example pattern taken along the line A-A' of FIG. 1.

FIG. 3 is a block diagram of a cross-sectional view of another example pattern 320 taken along the line A-A' of FIG. 1. In the embodiment of FIG. 3, the pattern 320 includes dots deposited over the substrate 110 and composed of a medium including a plurality of quantum dots that fluoresce the non-visible light in response to absorbing at least one of the non-visible light and the visible light. The quantum dots may be semiconductors having excitons confined in all three spatial dimensions. Properties of the quantum dots, such as the frequency of light fluoresced or emitted after excitation from absorbing at least one of the non-visible light and the visible light, may vary according to a size and shape of the quantum dots. For example, the quantum dots may be rectangular or triangular in shape and between 2 to 10 nanometers (nm) in diameter.

The dots of the pattern 220 and the dots of the pattern 320 in FIGS. 2 and 3 are shown to have a width of 80 micrometers or microns ($\mu$) and a height of $0.5\mu$. However, the dots of the pattern 220 and the dots of the pattern 320 may have widths greater or less than $80\mu$ and heights greater or less than $0.5\mu$. In addition, while the dots of the pattern 220 are shown to have a rectangular shape and the dots of the pattern 320 are shown to have a circular shape, the dots of the pattern 220 and the dots of the pattern 320 are not limited thereto and may be formed in a variety of shapes and sizes.

While the dots of the pattern 220 and the dots of the pattern 320 are shown separately in FIGS. 2 and 3, embodiments may include a combination of both of the dots of the pattern 220 and the dots of the pattern 320 over the substrate 110.

Figure 4:
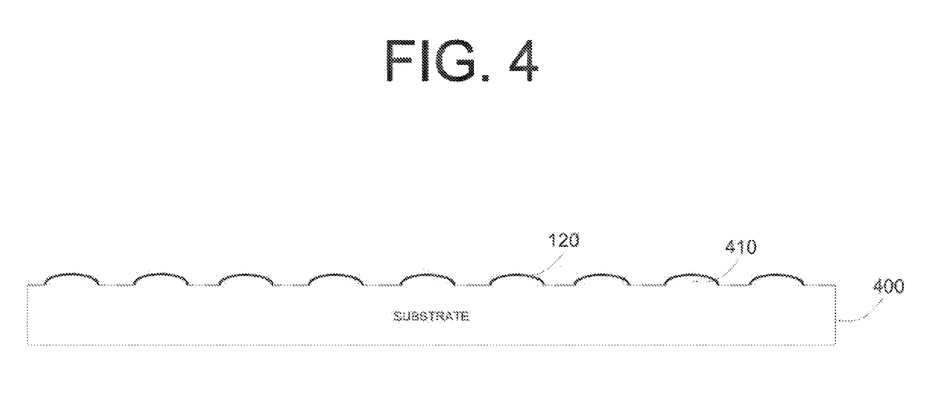
FIG. 4 is a block diagram of a cross-sectional view of an example substrate taken along the line A-A' of FIG. 1.
Figure 5:
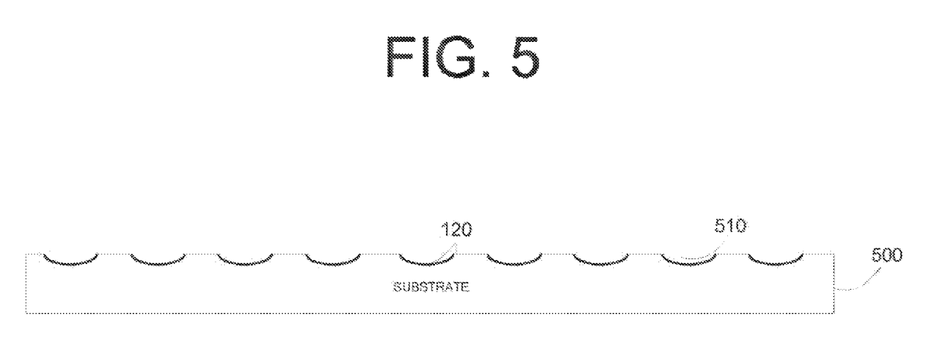
FIG. 5 is a block diagram of a cross-sectional view of another example substrate taken along the line A-A' of FIG. 1.

FIG. 4 is a block diagram of a cross-sectional view of an example substrate 400 taken along the line A-A' of FIG. 1. FIG. 5 is a block diagram of a cross-sectional view of another example substrate 500 taken along the line A-A' of FIG. 1. In. FIG. 4, the substrate 400 is shown to have a plurality of convex shapes 410, while in FIG. 5, the substrate 500 is shown to a have plurality of concave shapes 510. In FIGS. 4 and 5, the pattern 120 may be along a surface of the convex shapes 410 and the concave shapes 510. For example, the pattern 120 may be above the surface of the convex shapes 410 and below the surface of the concave shapes 510. The convex shapes 410 and the concave shapes 510 may allow the light to be more efficiently directed from the pattern 120 to, for example, a detector to detect the light. For example, a greater percentage of the non-visible light may reflect in a uniform or generally parallel direction from the pattern 120 in FIG. 4 or 5.

However, embodiments may also have the pattern 120 below the convex shapes 410 and above the concave shapes 510. Further, embodiments have may have only a single one of the concave and convex shapes 410 and 510 or a combination of the both concave and convex shapes. Moreover, other embodiments of the substrate 110 may also include shapes having various other types of raised or lowered surfaces, such as triangular or square shaped surfaces.

Figure 6:
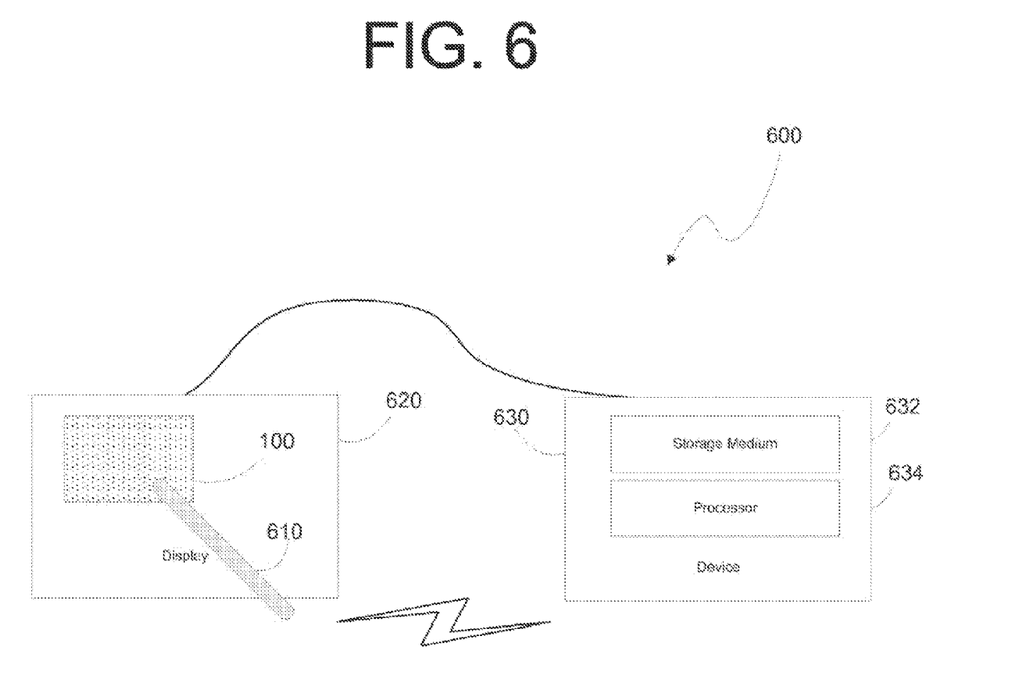
FIG. 6 is a block diagram of an example display system including the filter of FIG. 1.

FIG. 6 is a block diagram of an example display system 600 including the filter 100 of FIG. 1. In the embodiment of FIG. 6, the display system 600 includes a marking device 610, a display 620 behind the filter 100 of FIG. 1, and a computing device 630. The computing device 630 includes a processor 632 and a machine-readable storage medium 634.

The marking device 610, may be a writing utensil used by the user to write over the display 620, such as a stylus, to be used with the computing device 630 connected to the display 620. The marking device 610 may gather data relating to the user's movement of the marking device 610 over the display by determining a position of the marking device 610 relative the pattern 120 included in the filter 100 over the display 620. This data may then be transmitted to the computing device 630 and/or another device (not shown), either through wired or wireless communication. The marking device 610 will be explained in greater detail below, with respect to FIGS. 7 and 8.

The display 620 may include an integrated display device, such as a Liquid Crystal Display (LCD) panel or other type of display panel. The display 620 may also include one or more external display devices, such as an LCD panel, a plasma panel, a Cathode Ray Tube (CRT) display, or any other display device. The display 620 may be connected to the computing device 630 and may display information related the user's movement of the marking device 610 over the display 620. The user's movement of the marking device 610 may be communicated to the display 620 through the computing device 630. While the display 620 and the computing device 630 are shown to have a wired connection in FIG. 6, embodiments may also include other types of connections, such as wireless connections.

In FIG. 6, the computing device 630 is shown to be a desktop computer. However, embodiments of the computing device 630 may also include, for example, a notebook computer, an all-in-one system, a slate computing device, a portable reading device, a wireless email device, a mobile phone, and the like.

The processor 632 included in the computing device 630 may be one or more central processing units (CPUs), semiconductor-based microprocessors, and/or other hardware devices suitable for retrieval and execution of instructions stored in the machine-readable storage medium.

The machine-readable storage medium 634 included in the computing device 630 may be any electronic, magnetic, optical, or other physical storage device that contains or stores executable instructions. Thus, the machine-readable storage medium 634 may be, for example, Random Access Memory (RAM), an Electrically Erasable Programmable Read-Only Memory (EEPROM), a storage drive, a Compact Disc Read Only Memory (CD-ROM), and the like. The machine-readable storage medium 634 may store one or more applications executable by the processor 632. For example, the machine-readable storage medium 634 may include handwriting or graphic design applications for interpreting the user's movement of the marking device 620.

Figure 7:
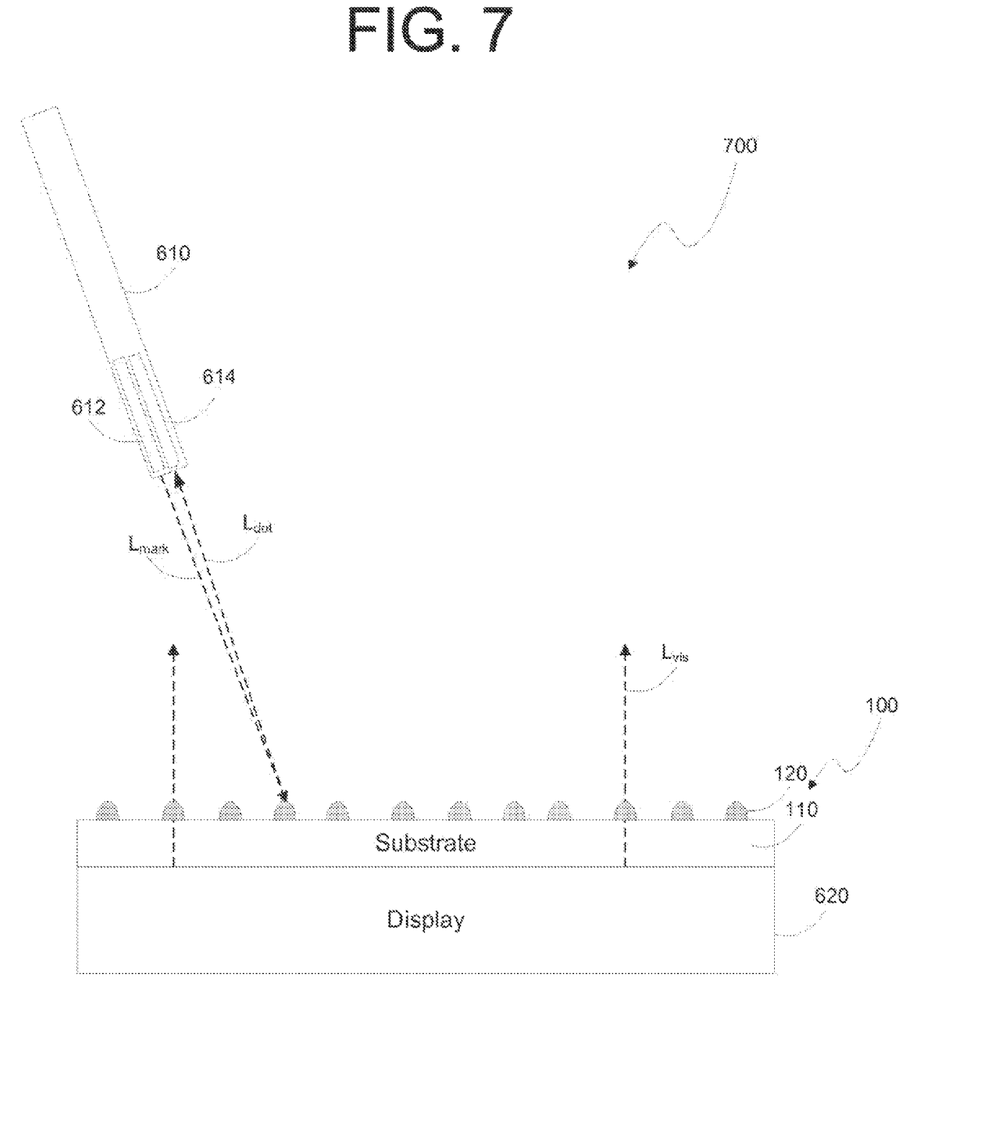
FIG. 7 is a more detailed block diagram of the display system of FIG. 6.

FIG. 7 is a more detailed block diagram of the display system of FIG. 6. In the embodiment of FIG. 7, the display system 700 includes the marking device 610, the filter 100 of FIG. 1 and the display 620 under the filter 100. The filter 100 includes the substrate 110 and the pattern 120. The pattern 120 may be one of a solution including a plurality of quantum dots 320, as shown in FIG. 3, and stacked layers of thin film 220, as shown in FIG. 2. The quantum dots fluoresce non-visible light in response to absorbing at least one of visible and non-visible light. The stacked layers of thin film 220 reflect the non-visible light and transmit the visible light. The display 620 projects the visible light $L_{vis}$ at the filter 100 from a boundary of the substrate 110.

The marking device 610 includes a projector 612 and a detector 614. As shown in FIG. 7, the projector 612 projects the non-visible light $L_{mark}$ at the filter 100 and the detector 614 detects the non-visible light $L_{dot}$ projected or returned from the filter 100. The non-visible light $L_{dot}$ projected or returned from the filter 100 may include light reflected from the dots 220 or light fluoresced from the dots 320. The projector 612 may include a non-visible light emitting source, such as a diode, where types of non-visible light may include ultraviolet (UV) or infrared (IR) light. For example, IR light may have a wavelength greater than around 700 nm and UV light may have a wavelength less than around 400 nm. The detector 614 may include a non-visible light detecting source, such as a camera.

In an embodiment, the projector 612 may project the non-visible light $L_{mark}$ in the IR spectrum, and the detector 614 may detect the non-visible light $L_{dot}$ in the IR spectrum reflected from the dots 220. In this embodiment, the projector 612 may include an IR diode and the detector may include an IR camera.

In another embodiment, the projector 612 may project the non-visible light $L_{mark}$ in the UV spectrum, and the detector 614 may detect the non-visible light $L_{dot}$ in the UV spectrum reflected from the dots 220. In this embodiment, the projector 612 may include a UV diode and the detector may include a UV camera. In embodiments, a protective coating (not shown) may also be applied over the filter 100.

As discussed above with respect to FIG. 2, the dots 220 allow substantially all the visible light to pass through the dots 220. Thus, if the dots 220 are used for the pattern 120 in FIG. 6, a tighter spacing of the pattern or dots 120, such as less than 0.25 mm apart, would not degrade image quality.

Moreover, the tighter spacing would allow the detector 614 to either view more of the dots 120 or decrease its field of view. Increasing the number of dots 120 viewable by the detector 614 may allow for greater tracking precision of the marking device 610. Therefore, higher speed or more detailed movements of the marking device 610 may be captured with fewer errors, such as during handwriting or graphic design. Alternatively, if the field of view of the detector 614 is reduced, a smaller and/or lower-cost detector may instead be included in the marking device 610, where the smaller detector would result in an overall reduced size of the marking device 610.

Figure 8:
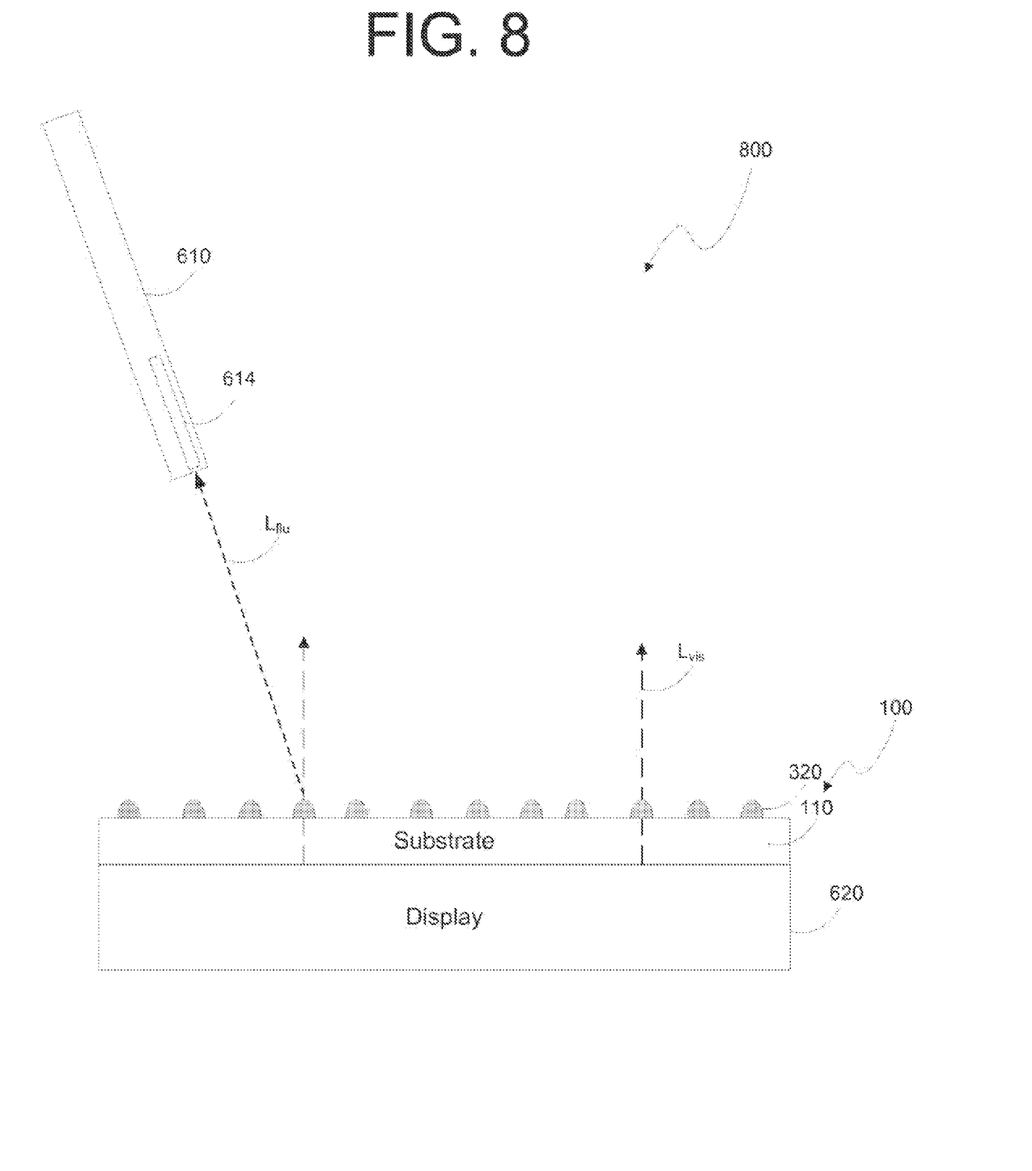
FIG. 8 is a block diagram of an example display system including the filter of FIG. 3.

FIG. 8 is a block diagram of an example display system 800 including the filter 300 of FIG. 3. The embodiment of FIG. 8 is somewhat similar to the embodiment of FIG. 7, except the marking device 610 does not include a projector and only the dots 320 may be over the substrate 110. Here, the detector 614 may detect the non-visible light $L_{flu}$, such as the IR light, fluoresced by the dots 320 in response to absorbing some of the visible light $L_{vis}$ emitted from the display 620. Thus, removing the projector may result in a marking device 610 of lower cost, smaller size, and reduced power consumption.

Depending on the properties of the quantum dots, the quantum dots may absorb both the visible and the non-visible light. However, the concentration of the quantum dots in each of the dots 320 of FIG. 3 or a density of the dots 320 over the display 620 may be varied so that a threshold percentage of the visible light is projected from the display 620 to the user, such that image quality of display 620 is not greatly reduced.

Figure 9:
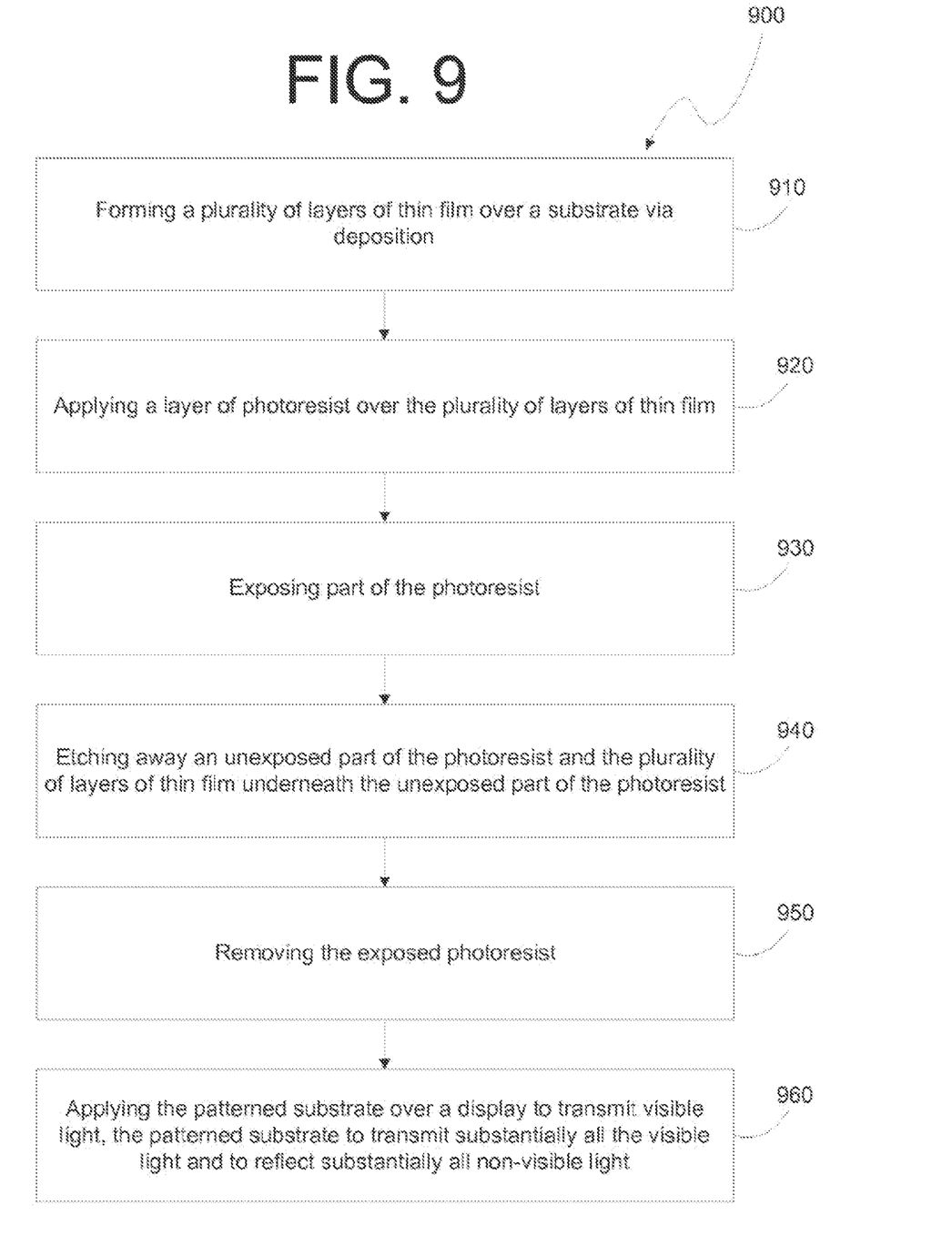
FIG. 9 is a flowchart of an example method for forming the filter according to the example pattern of FIG. 2.

FIG. 9 is a flowchart of an example method for forming the filter 200 according to the example pattern 220 of FIG. 2. In the embodiment of FIG. 9, at block 910, a plurality of stacked layers of thin film 222 and 224 are formed via deposition over the substrate 110. The stacked layers of thin film 222 and 224 may be formed at block 910 by chemical deposition, physical deposition, and the like. Chemical deposition may include, for example, chemical solution deposition (CSD), chemical vapor deposition (CVD), plasma enhanced CVD (PECVD), and the like. Physical deposition may include, for example, physical vapor deposition (PVD), with variants of PVD including cathodic arc deposition, electron beam physical vapor deposition, evaporative deposition, pulsed laser deposition, sputter deposition, and the like.

Forming the dots 220 via PVD may allow for a relatively large volume of the dots 220 to be formed at a relatively low cost. Further, production of the dots 220 may be readily scaled according to a manufacturer's or consumer's needs while still maintaining batch to batch or roll to roll consistency for PVD.

Then, at block 920, a layer of photoresist is applied over the plurality of layers of thin film 222 and 224 by, for example, spin coating. As the dots 220 are formed from the plurality of layers of thin film 222 and 224, the dots 220 reflect substantially all or at least a portion of the non-visible light.

Next, at block 930, part of the photoresist is exposed to an intense light, such as UV. Then, at block 940, an unexposed part of the photoresist and the plurality of layers of thin film 222 and 224 underneath the unexposed part of the photoresist are etched away using, for example, a liquid ("wet") or plasma ("dry") chemical agent. Afterward, at block 950, the exposed photoresist is removed to form the pattern 220, using, for example, a resist stripper that chemically alters the exposed photoresist so as not to adhere to the substrate or a plasma containing oxygen ("ashing").

Lastly, at block 950, the patterned substrate or filter 100 is applied over the display 620 that is to transmit visible light, the patterned substrate 100 to transmit substantially all the visible light and to reflect at least a portion or substantially all non-visible light from the projector 610.

Depending on a type of the pattern 120, the pattern 120 may be deposited differently. For example, according to an embodiment, a method for depositing the dots 320 of FIG. 3 may include applying a solution including a plurality of quantum dots over the substrate 110, where the quantum dots fluoresce the non-visible light in response to absorbing at least one of the non-visible light and the visible light. The application of the dots 320 may include printing, spraying or pipetting the solution including the quantum dots onto the substrate 110, or the like. Printing may include, for example, one or more ejection processes, such as one or more jetting processes, including thermal and/or piezo jetting, such as by use of an ink jet component.

After the solution is applied, the dots 320 may be allowed to dry or affix to the substrate 110. For example, if the dots 320 are applied to the substrate 320 via printing, a surface of the substrate upon which the dots 320 are printed is not disturbed for a threshold period of time. The threshold period of time may be a time period sufficient for the dots 320 to become affixed to the substrate 110.

The above method of FIG. 9 may be performed, for example, in a cleanroom using automated, mechanical tracking systems for coordination. The order of the blocks for the above method of FIG. 9 are not limited to the order shown. Additionally, intervening blocks not shown may be also employed in the above embodiments. Although a flowchart may describe the operations as a sequential process, many of the operations may be performed in parallel or concurrently. In addition, the order of the operations may be re-arranged. A process may be terminated when its operations are completed, but could have additional steps not included in the drawings.

According to the foregoing, embodiments disclosed herein provide to filter including a pattern that is to one of transmit substantially all visible light and fluoresce non-visible light, and the pattern is to reflect substantially all or a portion of the non-visible light if the pattern is to transmit substantially all the visible light. In this manner, according to an embodiment, a user may interact with a display that projects the visible light using a marking device that projects then non-visible light even when the pattern includes a relatively high density dots over the display. Thus, the user may carry out detailed or complex movements with the marking device over the display, such as in relation to handwriting capture or graphic design, without compromising image quality of the display. Moreover, the filter may be produced at a relatively high volume and relatively low cost.

We claim:

1. A filter for use with a display, comprising:
a substrate; and
a pattern of dots along a surface of the substrate, wherein the dots comprise a material to fluoresce non-visible light in a direction away from the display, in response to absorbing a portion of visible light from the display, and the pattern of dots is to transmit substantially all the visible light from the display.

2. A display system, comprising:
a display to project visible light; and
a filter to receive the visible light from the display, the filter comprising a substrate and a pattern of dots on the substrate, the dots comprising a material to fluoresce non-visible light in response to absorbing a portion of the visible light from the display, and the pattern of dots to transmit a remaining portion of the visible light through the filter and away from the display.

3. The display system of claim 2, wherein the dots comprise quantum dots.

4. The filter of claim 1, wherein an average length between adjacent dots of the dots of the pattern is less than 0.25 millimeters (mm).

5. The filter of claim 1, wherein the substrate includes at least one of a concave and convex shape and the pattern is along a surface of at least one of the concave and convex shapes.

6. The filter of claim 1, wherein the dots comprise quantum dots.

7. The filter of claim 1, wherein the material of the dots comprises a semiconductor having excitons that fluoresce the non-visible light in response to excitation from absorption of the portion of the visible light from the display.

8. The filter of claim 1, wherein the dots are convex dots.

9. The filter of claim 1, wherein the dots are concave dots.

10. The filter of claim 1, wherein the pattern of dots is to transmit substantially all the visible light from the display through the pattern of dots and away from the display.

11. The display system of claim 2, wherein the filter is attached to a surface of the display.

12. The display system of claim 2, wherein the pattern of dots is to fluoresce the non-visible light in a direction away from the display.

13. The display system of claim 12, further comprising a detector to detect the non-visible light fluoresced by the pattern of dots.

14. The display system of claim 13, further comprising a marker device including the detector, the marker device useable by a user for interaction with the display system.

15. The display system of claim 14, wherein the marker device is without a projector to project non-visible light.

16. The display system of claim 14, wherein the marker device includes a projector to project non-visible light towards the filter, and wherein the pattern of dots is to reflect the non-visible light from the projector.

17. The display system of claim 3, wherein the quantum dots are to fluoresce infrared light in response to absorbing the portion of the visible light.

18. A method comprising:
   forming quantum dots on a substrate; and
   applying the substrate with the quantum dots to a display that transmits visible light, the quantum dots to absorb a portion of the visible light from the display and to fluoresce non-visible light in response to the absorbing, and the pattern of dots to transmit a remaining portion of the visible light from the display in a direction away from the display.

19. The method of claim 18, wherein the quantum dots comprise a semiconductor having excitons that fluoresce the non-visible light in response to excitation from absorption of the portion of the visible light from the display.

\* \* \* \* \*